United States Patent
Reinhard et al.

[11] Patent Number: 6,065,270
[45] Date of Patent: May 23, 2000

[54] METHOD OF PRODUCING A FILLED PLASTIC SYRINGE BODY FOR MEDICAL PURPOSES

[75] Inventors: Michael Reinhard, Ober-Olm; Ralf Bouffleur; Michael Spallek, both of Ingelheim, all of Germany

[73] Assignee: Schott Glaswerke, Mainz, Germany

[21] Appl. No.: 08/993,621

[22] Filed: Dec. 18, 1997

[30] Foreign Application Priority Data

Dec. 18, 1996 [DE] Germany .......................... 196 52 708

[51] Int. Cl.[7] ........................................ B65B 3/02
[52] U.S. Cl. ........................ 53/426; 53/452; 53/471; 53/474; 53/476; 53/140
[58] Field of Search .............................. 53/426, 452, 467, 53/471, 473, 474, 476, 266.1, 284, 284.5, 140

[56] References Cited

U.S. PATENT DOCUMENTS

| | | | |
|---|---|---|---|
| 3,708,945 | 1/1973 | Klettke | 53/471 |
| 3,807,119 | 4/1974 | Shields | 53/471 |
| 3,826,059 | 7/1974 | Novitch | 53/426 |
| 3,919,374 | 11/1975 | Komendowski | 264/90 |
| 4,035,981 | 7/1977 | Braun et al. | 53/426 |
| 4,530,202 | 7/1985 | Powell et al. | 53/426 |
| 4,628,969 | 12/1986 | Jurgens, Jr. et al. | 141/1 |
| 4,671,763 | 6/1987 | Weiler | 425/525 |
| 4,718,463 | 1/1988 | Jurgens, Jr. et al. | 141/11 |
| 4,757,907 | 7/1988 | Hansen | 53/140 |
| 4,910,942 | 3/1990 | Dunn et al. | 53/426 |
| 4,995,511 | 2/1991 | Evans | 206/362.1 |
| 5,373,684 | 12/1994 | Vacca | 53/471 |
| 5,531,255 | 7/1996 | Vacca | 53/471 |
| 5,603,200 | 2/1997 | Calvano | 53/426 |
| 5,620,425 | 4/1997 | Heffernan et al. | 604/281 |
| 5,884,457 | 3/1999 | Ortiz et al. | 53/471 |

FOREIGN PATENT DOCUMENTS

E-68 979  7/1987  Austria .

OTHER PUBLICATIONS

Venten et al., "Eine neue Anlage zur Verarbeitung von Spritzampullen", *Pharm. Ind.*, vol. 40, No. 6, pp. 665–671, 1978. (with abstract).

*Primary Examiner*—Peter Vo
*Assistant Examiner*—Matthew Luby
*Attorney, Agent, or Firm*—McDonnell Boehnen Hulbert & Berghoff

[57] ABSTRACT

A method for manufacturing a filled syringe body within a single continuous manufacturing line in a self-contained environment with controlled conditions. The method includes the steps of injection molding the syringe body, sealing the one end of the syringe body, siliconizing the barrel of the syringe body, filling it, sealing the other end of the syringe, and sterilizing it. With this new "injection mold-fill-seal" method, a syringe body can be manufactured as a mass-produced article in one manufacturing line in an inexpensive manner.

31 Claims, 5 Drawing Sheets

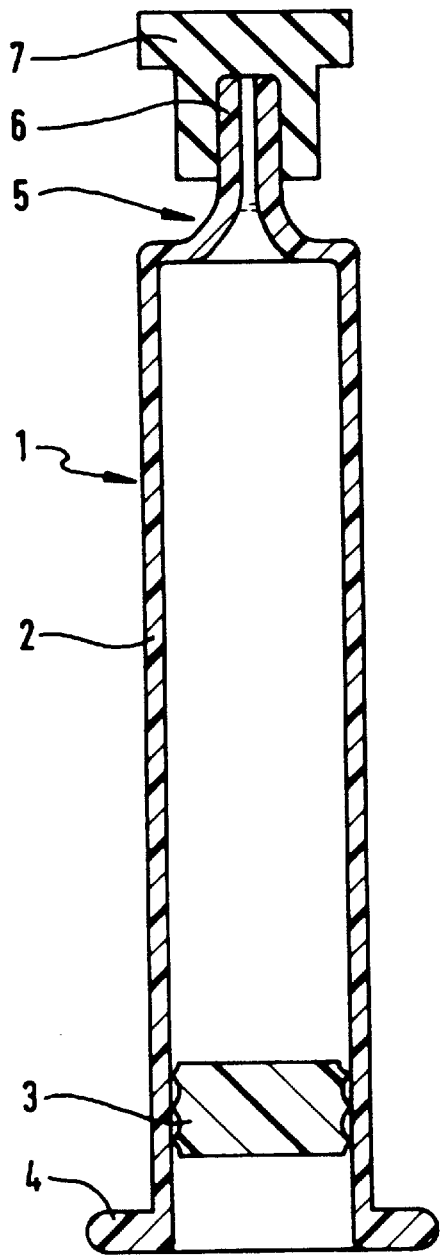
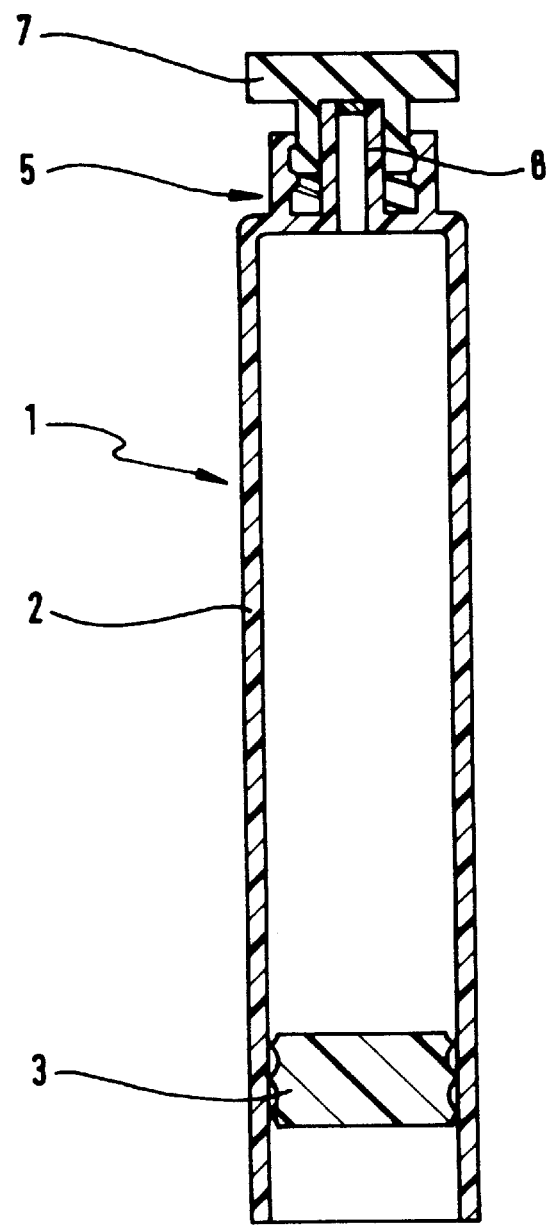
Fig. 1a
Fig. 1b

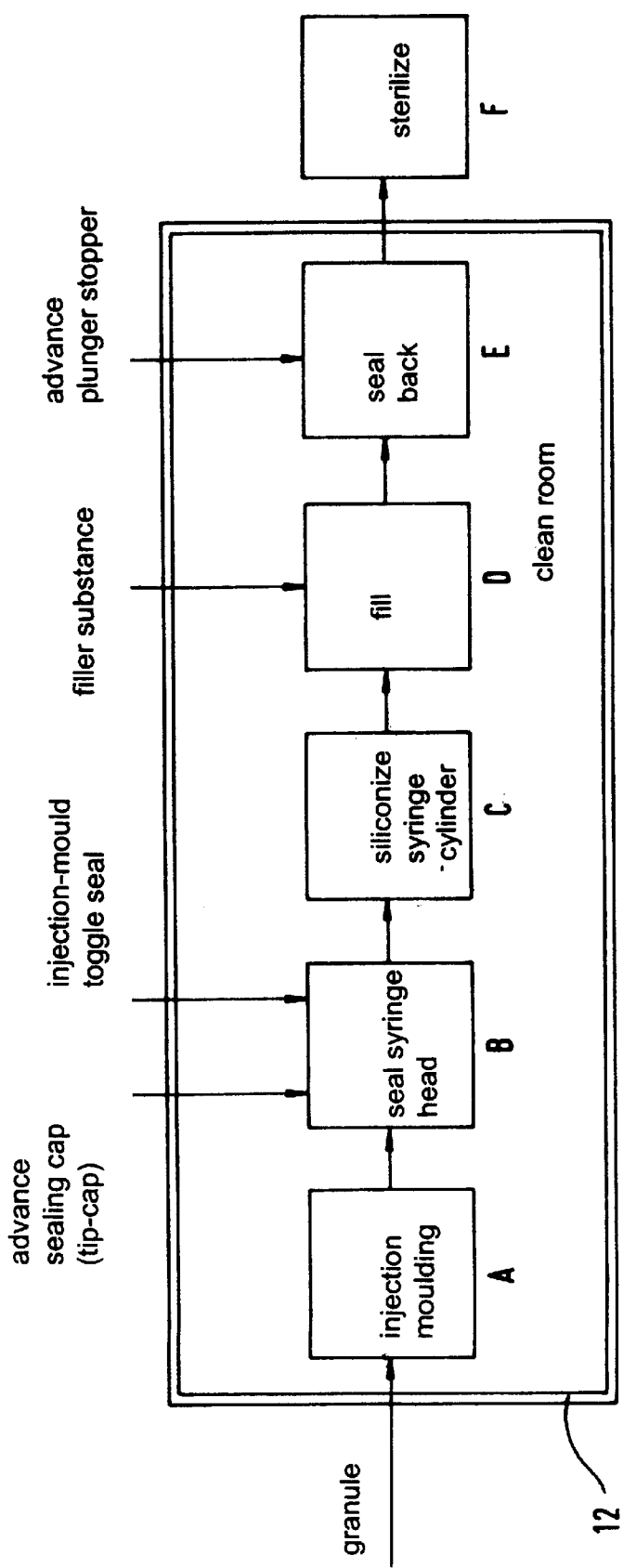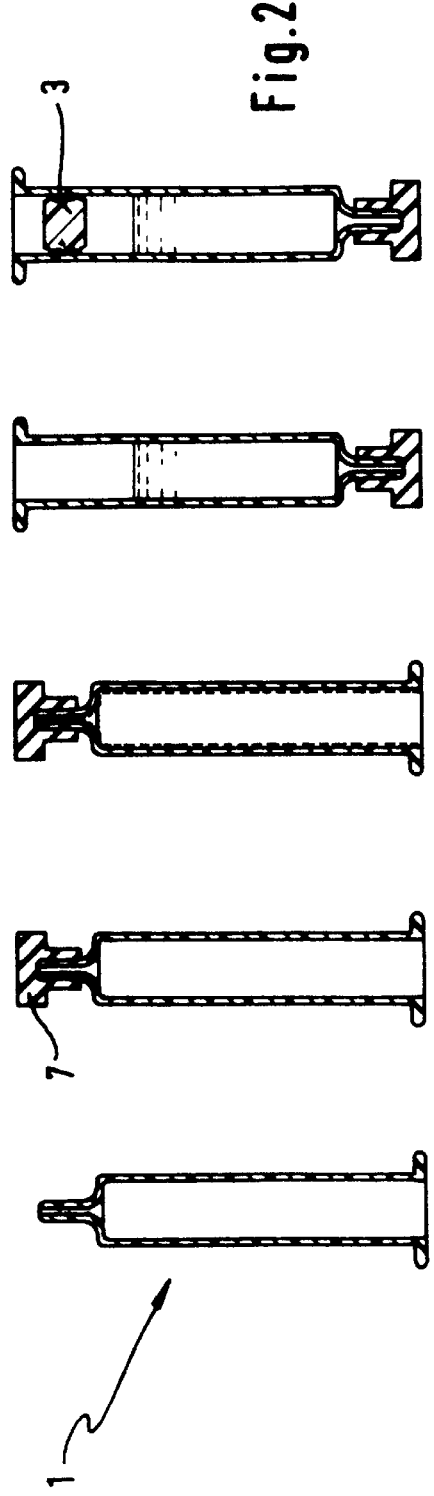
Fig. 2

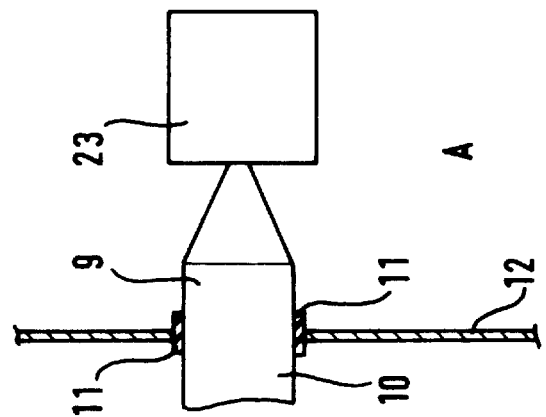
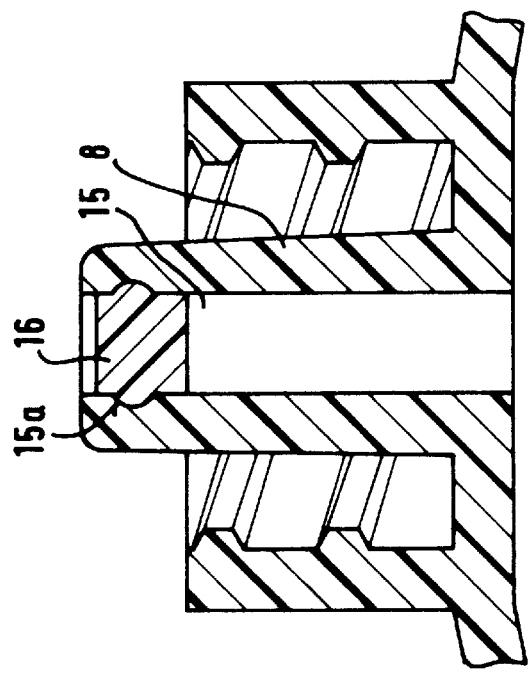
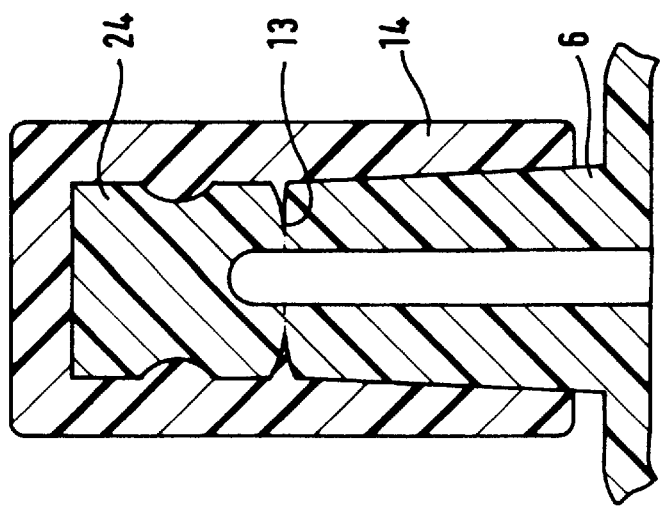

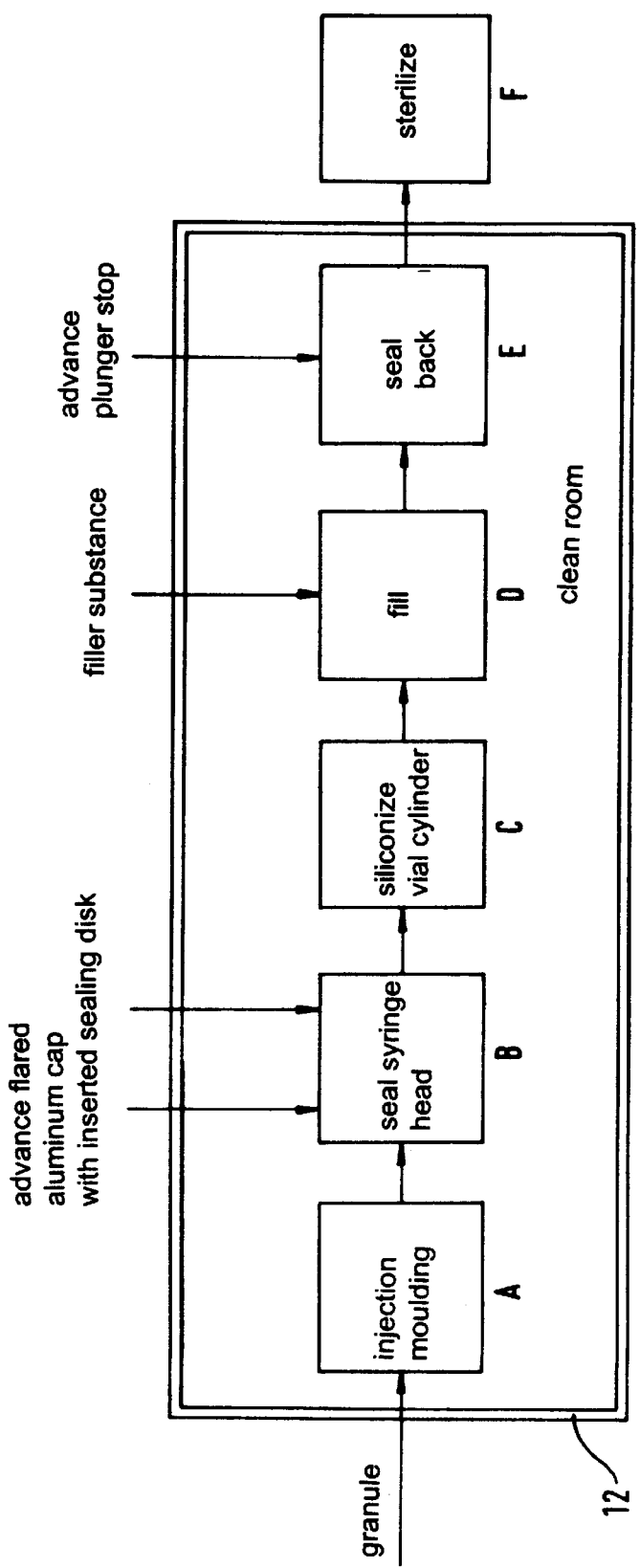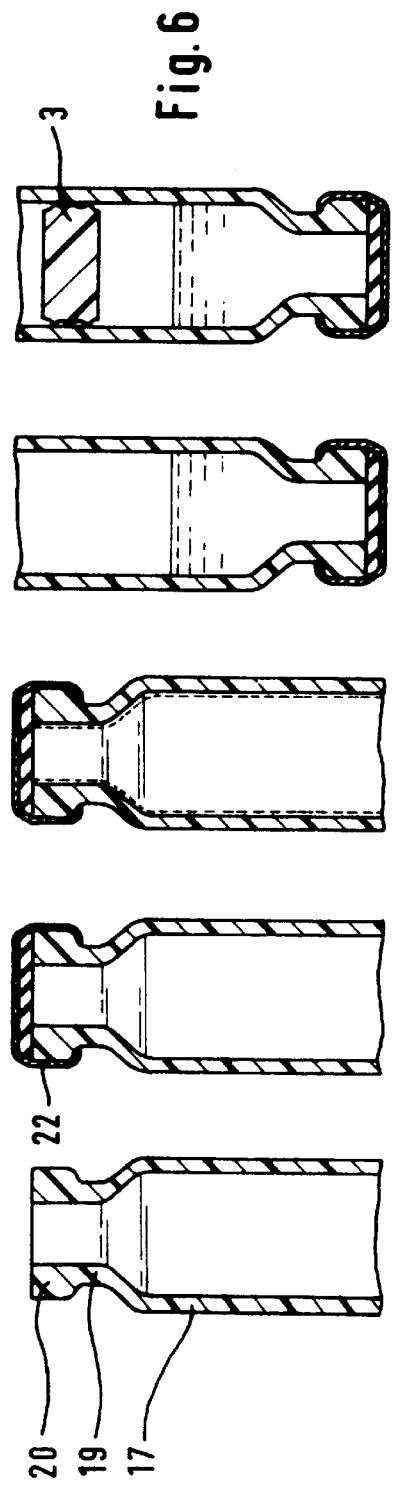
Fig. 6

METHOD OF PRODUCING A FILLED PLASTIC SYRINGE BODY FOR MEDICAL PURPOSES

This application claims foreign priority benefits under 35 U.S.C. §119(a)–(d) from German Patent Application No. 196 52 708.2 now German Patent 19652708C2.

BACKGROUND OF THE INVENTION

1. Field of the Invention

The invention relates to a method of producing a filled plastic syringe body for medical purposes. Such a syringe body consists of a syringe cylinder having two ends, an outlet end and a rear end. A plunger stopper is inserted into the rear end, thereby sealing it. The outlet end is provided with an integrally molded head designed to accommodate an application element. The head is sealed by means of a removable sealing element for storage.

Such a syringe body may be, for example, a syringe body for a filled plastic disposable syringe, also known as a ready-to-use syringe, such as those whose dimensions are defined in the standards DIN 13,098 for unfilled plastic disposable syringes and in DIN ISO 11,040, part 4, for prefilled glass syringes. The syringe body for these ready-to-use syringes consists of a syringe cylinder having a finger rest on the end that is sealed with the plunger stopper and a syringe head on its outlet end.

Such a syringe body may also be a syringe cylinder, which is similar to the syringe body for a finished, ready-to-use syringe, but without the finger rest. Such a syringe cylinder is referred to below as a syringe ampule.

Such a syringe body may also be a cartridge ampule such as those whose configuration is stipulated in the standards DIN ISO 11,040, parts 1–3, and DIN ISO 13,926-1 for cartridge ampules with glass cylinders. As indicated by these standards, the cartridge ampules generally belong to the "pre-filled syringe" category. They consist of a syringe cylinder, the cartridge ampule cylinder, having an integrally molded neck part on the outlet end with a flat mouth edge and an edge bead. The outlet end can be sealed tightly by a flanged aluminum cap and a washer. The other end of the cylinder can be sealed with a plunger stopper.

2. Background of the Related Art

Ready-to-use plastic syringes of the above-mentioned type, especially small-volume ready-to-use syringes with a volume preferably in the range of 1–10 mL, are usually manufactured by producing the syringe body in a production plant that processes plastics into pharmaceutical packages. The resulting syringe bodies, after intermediate storage, are then shipped to a pharmaceutical plant where they are filled and sealed tightly, ready for use.

Production of such a syringe body is disclosed, for example, by World Patent WO 95/12482 and by German Patent DE 4,438,360 A1. According to these references, the syringe body is first produced by injection molding, at least under clean room (low particle count) conditions, its inside wall is optionally siliconized, and the syringe head is sealed by a sealing cap, referred to as a tip-cap, which is made of a rubbery material. As a rule, the syringe body produced in this way is packaged hermetically in a low-particulate and bacteria-proof container at the end of the manufacturing process. The syringe body then undergoes a sterilization process, which is usually performed at another company. Gamma rays can be used for sterilization. The body is then ready for intermediate storage or for shipping to the filling plant. The filling and sealing operation at the pharmaceutical company of the ready-to-use syringe is described, for example, in the article by H. Dollinger, "Filling disposable syringes in a high-performance compact system," published in the journal *Die Pharmazeutische Industrie* [*The Pharmaceutical Industry*], vol. 56, no. 1 (1994), which describes the filling of ready-to-use glass syringes. Typical process steps include removal of the as-delivered syringe body, optional cleaning, drying and sterilizing, if the syringe body was not sterilized on delivery, filling and sealing the syringe body, in most cases in combination with sterilization of the filled syringe body, and labeling and further finishing for shipping to the consumer. The production and filling of plastic syringe ampules and plastic carpules are similar.

The above-mentioned interfaces between the manufacturer of the plastic packaging material (plastics processing plant), the plant which performs the sterilization of the empty packaging material and the filling pharmaceutical plant is disadvantageous for a variety of reasons. The main reasons are the additional required steps of shipping, packaging and unpackaging of the syringe elements, separation, quality assurance and the additional risks of microbiological and particulate contamination in storage and shipping of the unfilled syringe cylinders for the respective type of syringe body. For example, the syringe body could develop a static charge during shipping that could result in dust adhering to the body which would have to be removed before filling.

Furthermore, there is a considerable interface-related expense associated with cleaning, drying and sterilization. This expense is very high with a glass syringe body according to the related art cited above, although glass bodies (in contrast with plastic bodies) can still be dried relatively easily by using high temperatures. With plastic bodies, it is even more expensive. These expensive procedures are described, for example, in European Patent EP 227,401, which also defines a special washing process. Furthermore, for injection molding of syringe bodies, an internal core is necessary which results in intimate contact with the hot polymer melt and a friction process on the complete inside surface in extracting the core. This in turn creates abrasion particles and thus necessitates the expensive washing and depyrogenization methods described in the above-mentioned European patent.

It is also known in the packaging industry that the packaging body can be manufactured and also filled and sealed, ready for use, in a single closed manufacturing line, i.e., a line automated for one pass operation, under controlled ambient conditions.

One such method, which has become known by the term "blow-fill-seal," is described, for example, in U.S. Pat. Nos. 3,919,374, 4,671,763 and 4,995,511. In this method, heat-softened plastic granules are injected into a mold by extrusion blow molding. A pharmaceutical packaging body is produced thereby which is filled while still in the mold and then sealed tightly.

However, this blow molding method allows only low-temperature processing of soft plastic materials such as polypropylene and polyethylene. It is possible to manufacture only containers whose inside dimensions permit relatively large tolerances because a core that predetermines the inside dimension with a narrow tolerance cannot be used in the blow molding method. Thus, bottle-like containers which are filled and sealed immediately after unmolding, i.e., while still hot, are typically produced with the known blow molding method. The inside dimensions of such containers are subject to relatively large tolerances, although they are not critical for the functionality of the container.

Primary pharmaceutical packaging materials such as filled plastic syringes or vials cannot be manufactured by this known blow molding method because this type of pharmaceutical packaging requires a nondeformable plastic material and low tolerances in the inside container diameter to guarantee an adequate seal during storage of the filled syringes and vials. Such syringes and vials are typically stored for a year or more.

Thus, it is an object of the invention to control the method for producing a filled plastic syringe body in such a way that it can be carried out easily, while minimizing the logistics costs and improving the siliconization of the plastic syringe body.

SUMMARY OF THE INVENTION

There is a need in the art for a method for producing a filled plastic syringe body that can be performed without difficulty while minimizing logistics costs. Such a method should also improve the siliconization of the plastic syringe body.

The object of the present invention is achieved with the following process steps which are carried out in a controlled environment within a single continuous manufacturing line:

Manufacturing the plastic syringe body by injection molding in a suitably shaped cavity of the injection mold with preset inside dimensions by using a core;

Sealing one end of the plastic barrel of the syringe body;

Siliconizing the surface of the inside wall of the plastic barrel of the syringe body which is still hot and active from injection molding, or as an alternative, even before sealing one end;

Filling the plastic syringe body with the syringe contents through the other open end of the plastic barrel of the syringe body; and Sealing the other end of the barrel of the syringe body.

The filled plastic syringe body, which is a mass-produced product, can be manufactured especially easily in a process that minimizes logistics costs and is thus inexpensive, in one cycle, i.e., directly, so it is ready for use. Such a syringe body is manufactured through the method according to this invention with "injection molding, filling and sealing" in a continuous manufacturing line, by analogy with the "blow-fill-seal" method described above, which is also known as the "injection mold-fill-seal" method.

It is also especially advantageous in direct filling of the syringe body that the lubricant layer (typically silicone oil), which must be applied, can be applied directly to the surface which is still hot and active from the injection molding process. This leads to an improved surface adhesion of the lubricant and thus to a significantly lower release of lubricant or ingredients of the lubricant into the solution during storage.

This measure is possible only with in-line manufacturing because, if the syringe body were filled "out of house," it could develop a static charge. Dust would then be deposited on the siliconized surface and would be practically impossible to remove at the pharmacy.

With the in-line production according to this invention, the number of particles can also be reduced significantly by blowing out the interior of the syringe body with ionized particle-free air that causes a discharge of the plastic inside wall. However, this discharged condition persists for only a certain period of time, which is adequate for in-line production but is not adequate for "out-of-house" filling.

The present invention is also used to manufacture a plastic syringe body for a filled disposable syringe (ready-to-use syringe). Such a syringe consists of a plastic syringe body with a plastic barrel on whose rear end a finger rest is provided and on whose head outlet end a plastic syringe head with an adapter cone or a lockable conical connection is molded to accommodate the counterpart of the application element. As to the production of such a syringe, the object of the present invention is achieved according to a further embodiment of the invention with the following process steps which are carried out in a controlled environment within a single continuous manufacturing line:

Manufacturing the plastic syringe body by injection molding in a suitably shaped cavity of the injection mold with preset inside dimensions by using a core;

Applying the seal to the syringe head of the plastic syringe body;

Siliconizing the surface of the inside wall of the plastic barrel of the syringe body which is still hot and active from injection molding, or as an alternative, this may also be done before applying the seal;

Filling the plastic syringe body with the syringe contents through the rear open end of the plastic barrel of the syringe body; and Sealing the rear open end of the plastic barrel of the syringe body with a plunger stopper.

Thus, filled disposable syringes (ready-to-use syringes) can be manufactured especially easily and thus inexpensively with the help of this method.

According to a further embodiment of the invention, the syringe ampules are manufactured following the above process steps.

The present invention is also used to manufacture a plastic syringe body for a filled cartridge ampule. Such a cartridge ampule consists of a plastic cartridge ampule cylinder as the barrel of the syringe, which is sealed with a plunger stopper at the rear end and has a molded neck part with a flat mouth edge and an edge bead on the outlet end. The outlet end is sealed tightly with a flanged aluminum cap and an inserted washer. As to the production of such an ampule, the object of the present invention is achieved according to another embodiment of the invention with the following process steps, which are carried out in a controlled environment within the single continuous manufacturing line:

Manufacturing the plastic cartridge ampule body by injection molding in a suitably shaped cavity of the injection mold with the inside dimensions predetermined by using a core;

Sealing the neck part with the externally applied flanged aluminum cap and an inserted washer;

Siliconizing the surface of the inside wall of the plastic barrel of the cartridge ampule which is still hot and active from injection molding, or as an alternative, this may be done before applying the flanged aluminum cap and the washer;

Filling the plastic barrel of the cartridge ampule with the syringe contents through the rear open end of the plastic barrel of the cartridge ampule; and Sealing the rear end with a plunger stopper.

Thus, cartridge ampules can be manufactured especially inexpensively by means of the method according to this invention.

In special cases, it may be advantageous not to fill the plastic syringe body through the rear end, but rather from the head end. According to another embodiment of the invention, this method is carried out in such a way that the rear end of the barrel of the plastic syringe or cartridge ampule is first sealed, the barrel is then filled through the head outlet end and finally the head outlet end is sealed.

Various options for sterilizing the filled plastic syringe body exist. Depending on the solution with which the barrel is filled, the sterilization may be performed either by autoclaving or by means of a suitable high-energy radiation such as gamma radiation, microwaves, beta rays or flashes or light. These sterilization steps may be eliminated when the process steps, including sealing the filled syringe body, are carried out under aseptic ambient conditions. After filling and sealing and optionally separately sterilizing the syringe body, it is labeled and finished for shipping.

In the case of the plastic ready-to-use syringe and the syringe ampule, the seal can be applied to the syringe head of the syringe body in various ways. A number of options are available here for those skilled in the art. Customer desires and consumer habits are also relevant to the decision in making a selection.

In the simplest case, a sealing cap made of a rubbery material, a so-called tip cap, is used as the sealing element. The tip cap can be supplied as a separate part, but may also be produced by molding it directly within the closed controlled volume as part of the injection molding process. As an alternative, a toggle closure of soft plastic with a break-off tip may also be used.

An especially advantageous method of applying the seal can be achieved by molding a toggle closure onto the syringe in the form of a sealing nipple made of a hard plastic material with a predetermined breaking point as part of the injection molding process. A protective cap of a soft elastic plastic is then molded onto it.

A further alternate manner of applying the seal involves directly sealing the outlet channel of the syringe in a form-fitting manner by means of a plug, preferably made of plastic.

BRIEF DESCRIPTION OF THE DRAWINGS

This invention will now be explained in greater detail with respect to the embodiments illustrated in the figures.

FIGS. 1a and 1b depict two embodiments of a syringe body produced by the method according to this invention, namely a syringe body of a ready-to-use syringe with a Luer-Lok cone in FIG. 1a and a syringe ampule with a lockable conical connection in FIG. 1b.

FIG. 2 is a schematic diagram of the individual process steps of the method according to this invention for production of ready-to-use syringes according to FIG. 1a.

FIGS. 3a and 3b depict two additional embodiments for sealing the syringe head of a ready-to-use syringe or a syringe ampule.

FIG. 4 depicts an embodiment for partially accommodating the injection molding machine in a controlled environment.

FIG. 6 is a schematic diagram of the individual process steps of the method according to this invention for producing the cartridge ampule of FIG. 5.

DETAILED DESCRIPTION OF THE INVENTION

Figure 5:
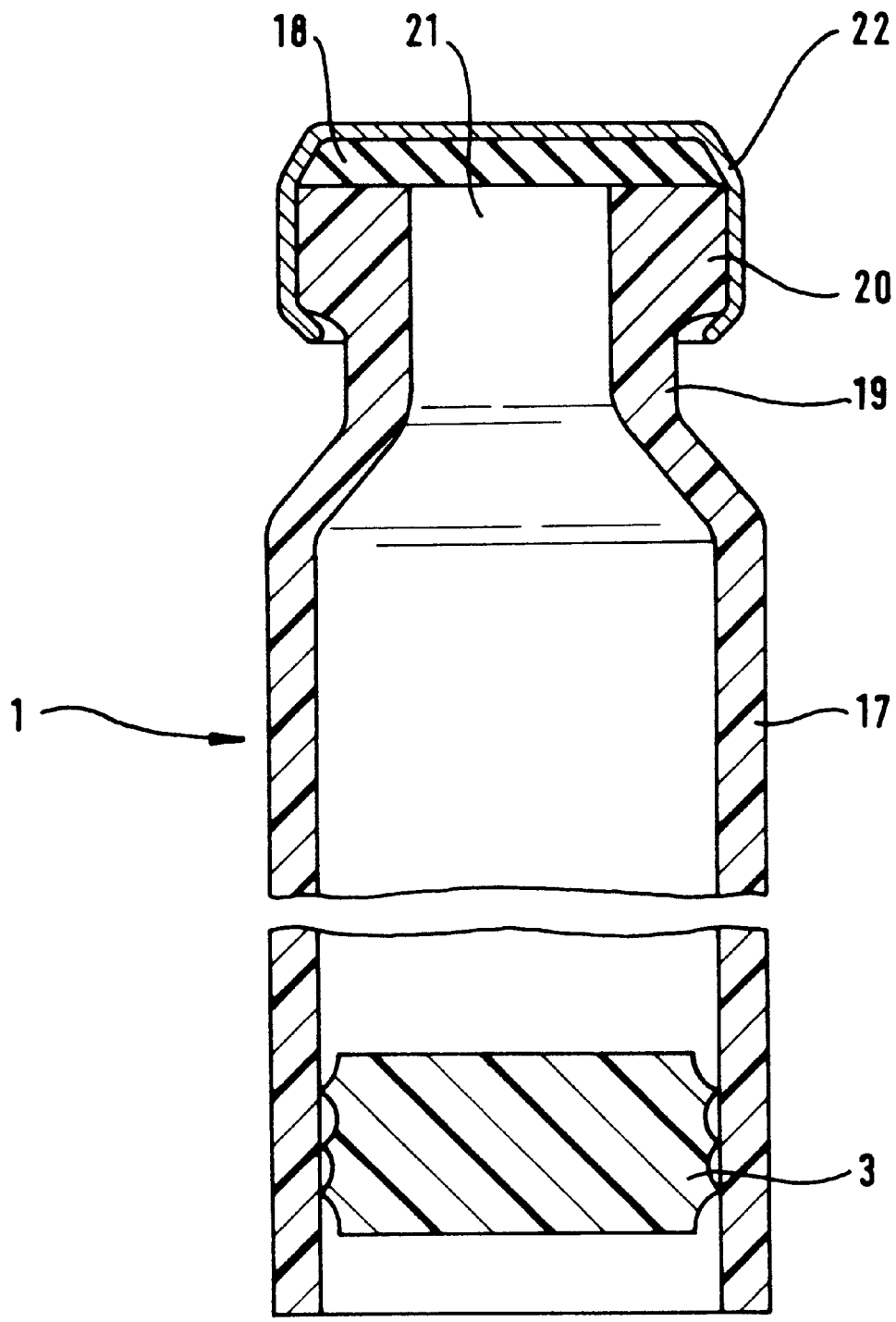
FIG. 5 depicts another embodiment of the filled syringe body in the form of a cartridge ampule.

The filled plastic ready-to-use syringe illustrated in FIG. 1a with a configuration according to DIN ISO 11040-4 for glass has a syringe body, which is labeled generally as 1. This syringe body is composed of a syringe barrel 2 which is sealed at one end with a movable plunger stopper 3 on which a plunger rod (not shown) can be applied in a known manner in use.

Furthermore, a conventional finger rest 4 is molded on syringe barrel 2, as shown in FIG. 1a. In an alternate equivalent embodiment, this finger rest may be attached subsequently as a separate part. For this purpose, an annular groove (not shown) may be provided on the rear end of the barrel of the syringe to simplify the attachment of the finger rest. Form-fitting snap closures with an undercut may also be provided, optionally in combination with an inserted securing ring, according to German Patent DE 4,434,644 A1 (FIGS. 1b and 1c).

This finger rest 4 is not provided on the filled pharmaceutical packing body of FIG. 1b, which is referred to as a "syringe ampule" instead of the syringe body of FIG. 1a. With the exception of the finger rest, the syringe ampule has the same configuration as the syringe body of FIG. 1a. The same reference numerals are used to denote similar parts.

As shown in FIG. 1a, the outlet end of barrel 2 of the syringe is provided with a molded syringe head 5 that includes a Luer-Lok cone 6. Similarly, the outlet end of the barrel 2 of the syringe ampule of FIG. 1b is provided with a lockable conical connector 8 (Luer-Lok). The connector 8 is shown in detail in FIG. 3b. When used, a standard needle with a fitted attachment (not shown) can be attached to this Luer-Lok cone 6 in a known way. Accordingly, the lockable conical connection 8 in FIG. 1b can be connected with the respective mating piece attached to an infusion line. Details with respect to such an attachment are described in ISO standard 594, parts 1 and 2.

Syringe head 5 is sealed tightly by means of a sealing element 7. A sealing element in the form of a separate sealing cap, the tip cap, made of a rubbery material is shown in FIGS. 1a and 1b. In an alternate, equivalent embodiment, a so-called toggle closure, which is favorable from a manufacturing standpoint because it can be produced by direct injection molding, may also be provided. It is also possible to provide a closure according to FIGS. 3a and b, which is explained in greater detail below.

The ready-to-use syringe shown in the enlarged diagram in FIG. 1a, or the syringe ampule, shown in FIG. 1b, preferably has a volume in the range of 0.5–1.0 mL in this embodiment. Either syringe can be filled with solvents suitable for medical purposes for dissolving powdered medications, pharmaceuticals or diagnostic agents. These solvents include water for injection, saline solution, water with bacteriostatic additives or with medically active substances, 0.3% sodium chloride solution, and a local anesthetic for dental medicine or a preparation containing insulin.

The syringe body is made of a plastic which must generally be clear and transparent, suitable for autoclaving or sterilizing with steam or high-energy radiation, and must at least form a barrier against water vapor diffusion so the syringe body can be stored for long periods of time, i.e., the loss of water and the related increase in concentration is acceptable. Preferably the syringe body is made of a cyclic olefin copolymer (COC). This material provides an excellent barrier to water vapor in addition to having the required mechanical strength and being clear and transparent. The syringe body could be produced in several layers with different plastics or separate barrier layers could be introduced, as described in German Patent DE 4,438,360 A1, whose disclosure is hereby incorporated by reference.

The process sequence with process steps A–F in the production of the filled syringe body of FIG. 1a will now be explained with reference to FIG. 2. The process steps for the production of the syringe ampule of FIG. 1b are similar.

Process steps A–E in this embodiment are carried out in a dust-free room such as a so-called clean room which has minimal particulate matter. Here, the room is represented by the double line border. If the clean room also has a low microbial content, it is referred to as a sterile room. However, it does not need to be a specific room of a building or an accessible compartment. In general, it is a sealed area with controlled ambient conditions and a controlled volume. This area may also be a so-called isolator, a narrowly defined encapsulated chamber with a small controlled volume.

The lower part of FIG. 2 illustrates the individual process steps on the basis of the syringe diagramed in the respective manufacturing condition. Process steps A–F take place according to this invention in a single continuous manufacturing line so that external interfaces are avoided.

In step A, the injection molding step, syringe body 1 is produced by injection molding in a clean room-ready injection molding machine. This machine receives the granular injection molding material from an external source in the usual manner. This injection molding, where the injection molding material is plastified by means of an injection unit and injected in a metered amount into a molding cavity of an injection mold, is the relevant state of the art and therefore need not be explained in greater detail.

As an alternative to the embodiment of FIG. 2, where the entire injection molding machine is within the controlled volume, the arrangement according to FIG. 4 can also be embodied in such a way that only the shaping injection mold 23 and the nozzle end 9 of the elongated injection molding unit are in the controlled volume. Sealing elements 11 in the border 12, which is indicated symbolically, prevent the conditions in the controlled volume from being exposed to negative external influences. The temperature prevailing in the injection molding unit 10 for plastifying the injection molding material ensures that the shaped syringe body will be free of germs (sterile) and free of pyrogens as required for pharmaceutical use.

In step B, the syringe head sealing step, closure 7 is placed on the syringe head of the syringe body. In this embodiment, a sealing cap (tip cap), which has optionally been sterilized, is placed on the syringe head. In an alternate, equivalent embodiment, a toggle closure with a predetermined breaking point made of an elastic or soft plastic material such as polyethylene may also be molded on the head, shown here as part of the injection molding method. Injection molding of the toggle closure may be done in the same injection mold in which the syringe body is molded, with a supply of a second plastic material (step A). In a further alternate, equivalent embodiment, the tip cap may also be molded directly on the syringe head with a thermoplastic elastomer.

FIG. 3a shows another possibility of sealing the syringe in an embodiment with an original seal. The details of the Luer-Lok cone 6 of FIG. 1a are shown in FIG. 3a. The cone is sealed with a toggle closure in the form of a molded sealing nipple 24 of hard plastic such as a COC with a predetermined breaking point. In addition, a covering or protective cap 14 made of a soft elastic plastic, preferably a thermoplastic elastomer (TPE), may also be molded on to ensure the sterility of the Luer-Lok cone and the predetermined breaking area. To use the syringe, this cap is then twisted off together with the sealing nipple 24 that breaks at the predetermined breaking point FIG. 3b shows in detail another possible closure the lockable conical connection of FIG. 1b. The syringe is closed by partially filling the outlet channel 15 of the syringe head with a soft elastic plastic 16. A form-fitting connection is then established through an annular grove 15a in the channel. This sealing can be accomplished either by injection molding of an elastomer (TPE) or by inserting a prefabricated part. In use, this sealing part 16 is not removed, but instead it is punctured by the needle through a suitable cannula with a double-sided ground joint. Such a closure 16 may also be provided in the syringe body of FIG. 1a.

In step C, the siliconizing step, the inside wall of the barrel of the syringe is siliconized by conventional methods. In an alternate, equivalent embodiment, step C of the process may be carried out before step B.

In step D, the filling step, the syringe body is filled with the respective substance, which is supplied from an external source.

In step E, the rear end sealing step, the open rear end of the barrel of the syringe is sealed with the plunger stopper 3, which is preferably supplied as a separate sterile element from the outside. In an alternative, equivalent embodiment, the plunger stopper can be produced by injection molding directly in the barrel of the syringe.

In step F, the sterilization step, the filled and completely sealed ready-to-use syringe is subjected to a sterilization process. If the filling material has adequate thermal stability, sterilization can be accomplished easily by autoclaving. If the filling material is not heat resistant, sterilization is preferably performed by high-energy radiation, especially gamma radiation. Sterilization could also be performed by irradiation with microwaves.

Step F may be eliminated if steps A–E are carried out in a sterile room, i.e., in a clean room which is also sterile. This additional condition increases the protection from germs. If the controlled area is an encapsulated chamber as mentioned above, it can be sterilized easily with steam, $H_2O_2$ or any other appropriate media In many cases, it may be advantageous to fill the syringe body 1 through the orifice in the syringe head after first sealing the rear open end of the barrel of the syringe with the plunger stopper. The syringe head is then provided with closure 7. The corresponding process steps would take place in the order of steps E, D and B.

The method illustrated in FIG. 2 can also be used for plastic syringe barrels that are designed as cartridge ampules, according to the standards cited above. Such a filled cartridge ampule is shown in detail in FIG. 5. The respective manufacturing process is depicted in FIG. 6.

FIG. 5 shows a filled plastic cartridge ampule consisting of a barrel 17 which is sealed at the bottom end by a plunger stopper 3. At the outlet end, barrel 17 has a molded neck part 19 with an edge bead 20. The outlet orifice 21 has a flat mouth edge that is sealed tightly by means of a flanged aluminum cap 22, flanged on edge bead 20, and an inserted washer 18.

The respective manufacturing process is shown in FIG. 6, which is similar to FIG. 2. In step A, the injection molding of plastic cylinder 17 is performed with neck part 19 and edge bead 20. In step B, the barrel is sealed with the externally supplied and optionally sterilized aluminum flanged cap 22 accompanied by washer 18. In step C, the inside wall of the barrel 17 of the cartridge ampule is siliconized, followed by filling in step D. In step E, the barrel is sealed with plunger stopper 3, which is either supplied from an external source and optionally sterilized or is produced by injection molding in the clean room.

The other measures are the same as in the case of FIG. 2, including the variants described there. Specifically, step C can be performed before step B. Also, the sequence of filling and sealing can take place in the order of steps E, D and B.

Filling volumes of 1–50 mL and even more can be achieved by varying the diameter/length ratio of the barrel 17 of the cartridge ampule. Typical filling volumes are 1.5 mL and 3 mL.

The filled cartridge ampule barrels 17 can either be inserted into the syringe frame (e.g., for use for local anesthesia in dental medicine) or in so-called pen systems (e.g., for injecting insulin).

It should be understood that various changes and modifications to the preferred embodiments described herein will be apparent to those skilled in the art. Such changes and modifications can be made without departing from the spirit and scope of the instant invention and without diminishing its attendant advantages. It is therefore intended that such changes and modifications be covered by the appended claims.

What is claimed is:

1. A method of manufacturing a filled plastic syringe body for medical purposes, the syringe body comprising a barrel having a rear end which is open and an outlet end with a head molded thereon and designed to accommodate an injection element, a plunger stopper for insertion into the rear end of the barrel to seal it, and an element for sealing the head, the method of manufacturing the syringe body including the steps of:
   a. forming the syringe body by injection molding a material into a core in a cavity of an injection mold, the mold having shape and preset inside dimensions;
   b. opening and mold and removing the formed syringe body, said body having an initial temperature;
   c. sealing one end of the barrel of the plastic syringe body;
   d. siliconizing an inside wall surface of the barrel of the plastic syringe body immediately after the body is formed and while the body remains substantially at said initial temperature;
   e. filling the plastic syringe body through the other end of the barrel of the plastic syringe body; and
   f. sealing the other end of the barrel of the plastic syringe body,
   wherein the method is carried out in a controlled environment within a single continuous manufacturing line.

2. The method of claim 1 wherein the siliconizing step is performed before step (c).

3. The method of claim 1 wherein step (c) further comprises sealing an outlet end of the barrel by applying a closure to a head on the outlet end of the barrel of the syringe body.

4. The method of claim 3 wherein the closure is applied to the outlet end by attaching a sealing cap made of a soft elastic material.

5. The method of claim 3 wherein the closure is applied to the outlet end by molding a sealing cap made of a soft elastic material.

6. The method of claim 3 wherein the closure is applied to the outlet end by integrally molding a toggle closure with a predetermined breaking point, the closure made of a soft plastic material.

7. The method of claim 6 wherein the toggle closure is injection molded with a different plastic material than the plastic material from which the syringe body is molded, the toggle closure being injection molded in the same injection mold in which the syringe body is molded.

8. The method of claim 3 wherein the closure is applied on the outlet end by integrally molding a toggle closure in the form of a sealing nipple made of hard plastic material with a predetermined breaking point.

9. The method of claim 8 further comprising the step of molding a protective cap made of a soft elastic plastic over the nipple.

10. The method of claim 3 wherein the closure is sealed in a form fitting manner by means of a plug.

11. The method of claim 1 wherein the filling step further comprises filling the syringe body through a rear, open end of the barrel.

12. The method of claim 11 wherein step (f) further comprises sealing the rear, open end of the barrel of the syringe body with a plunger stopper.

13. The method of claim 12 wherein the plunger stopper is injection molded directly in the barrel.

14. The method of claim 1 wherein step (c) further comprises sealing a neck part of an outlet end of the barrel with a flanged aluminum cap and a washer.

15. The method of claim 14 wherein the filling step further comprises filling the syringe through a rear, open end of the barrel.

16. The method of claim 15 wherein step (f) further comprises sealing the rear, open end of the barrel of the syringe body with a plunger stopper.

17. The method of claim 1 wherein step (c) further comprises sealing a rear end of the barrel, the filling step farther comprises filling the barrel through an outlet head end, and step (f) further comprises sealing the outlet head end.

18. The method of claim 1 wherein the steps are carried out in a controlled environment designed as a sterile room.

19. The method of claim 1 further including the step of sterilizing the syringe body.

20. The method of claim 19 wherein the sterilization is accomplished by autoclaving.

21. The method of claim 9 wherein the sterilization is performed by high-energy radiation.

22. The method of claim 1 further including the steps of labelling and of finishing the filled and sealed syringe body.

23. The method of claim 1 wherein the barrel of the syringe body is filled with a solvent used for dissolving a powdered pharmaceutical or diagnostic agent.

24. The method of claim 23 wherein the solvent comprises: water, 0.3% sodium chloride solution, a local anesthetic for dental medicine or a preparation containing insulin.

25. The method of claim 1 wherein the manufactured syringe body is a disposable, ready-to-use syringe having a finger rest and an adapter cone or lockable conical connection.

26. The method of claim 1 wherein the manufactured syringe body is a syringe ampule having an adapter cone or a lockable conical connection.

27. The method of claim 1 wherein the manufactured syringe body is a cartridge ampule having a molded neck part with a flat mouth edge and an edge bead which is sealed by a flanged aluminum cap and an inserted washer.

28. The method of claim 21 wherein the sterilization is performed by using gamma rays.

29. A method of manufacturing a filled plastic syringe body for medical purposes, the syringe body comprising a barrel having a rear end which is open and an outlet end with a head molded thereon and designed to accommodate an injection element, a plunger stopper for insertion into the rear end of the barrel to seal it, and an element for sealing the head, the method of manufacturing the syringe body including the steps of:

a. forming the syringe body by injection molding a material into a core in a cavity of an injection mold, the mold having a shape and preset inside dimensions;
c. sealing the open rear end of the barrel of the plastic syringe body;
d. siliconizing an inside wall surface of the barrel of the plastic syringe body immediately after the body is formed and while the body remains substantially at said initial temperature;
e. filling the plastic syringe body through the outlet end of the barrel of the plastic syringe body; and
f. sealing the outlet end of the barrel of the plastic syringe body, wherein the method is carried out in a controlled environment within a single continuous manufacturing line.

30. The method of claim 29 wherein the siliconizing step is performed before step (c).

31. The method of claim 29 wherein step (f) further comprises applying a closure on the outlet end of the barrel of the syringe body.

* * * * *